(12) United States Patent
Henn

(10) Patent No.: US 6,770,280 B1
(45) Date of Patent: Aug. 3, 2004

(54) TREATMENT OF MENORRHAGIA, HYPERMENORRHEA, DYSMENORRHEA AND MENSTRUAL MIGRAINES BY THE ADMINISTRATION OF AN ANTIBACTERIAL MILK PRODUCT

(75) Inventor: Dale R. Henn, Minneapolis, MN (US)

(73) Assignee: Humanetics Corporation, Chauhassen, MN (US)

(*) Notice: Subject to any disclaimer, the term of this patent is extended or adjusted under 35 U.S.C. 154(b) by 225 days.

(21) Appl. No.: 09/683,070

(22) Filed: Nov. 15, 2001

(51) Int. Cl.$^7$ .......................... A61K 35/20; A61K 39/40; A61K 39/42; A61K 39/395

(52) U.S. Cl. .............................. 424/157.1; 424/130.1; 424/535

(58) Field of Search .......................... 424/130.1, 157.1, 424/535, 93.1, 93.4, 9.2, 184.1, 201.1, 203.1, 823; 435/7.1, 7.2, 7.32, 41, 71.1, 170, 243, 252.1, 822

(56) References Cited

U.S. PATENT DOCUMENTS

| | | | |
|---|---|---|---|
| 3,282,969 A | 11/1966 | Boswell | |
| 4,585,651 A | 4/1986 | Beck et al. | 424/88 |
| 4,636,384 A | 1/1987 | Stolle et al. | 424/87 |
| 4,732,757 A | 3/1988 | Stolle et al. | 424/87 |
| 4,732,763 A | 3/1988 | Beck et al. | 424/433 |
| 4,748,018 A | 5/1988 | Stolle et al. | 424/87 |
| 4,756,907 A | 7/1988 | Beck et al. | 424/85 |
| 4,879,110 A | 11/1989 | Beck et al. | 424/85.8 |
| 4,897,265 A | 1/1990 | Stolle et al. | 424/87 |
| 4,919,929 A | 4/1990 | Beck | 424/88 |
| 4,956,349 A | 9/1990 | Beck | 514/54 |
| RE33,403 E | 10/1990 | Stolle et al. | 424/87 |
| RE33,565 E | 4/1991 | Stolle et al. | 424/87 |
| 5,106,618 A | 4/1992 | Beck et al. | 424/85.8 |
| 5,128,127 A | 7/1992 | Beck | 424/88 |
| 5,194,255 A | 3/1993 | Beck et al. | 424/87 |
| 5,242,691 A | 9/1993 | Beck | 424/535 |
| 5,288,496 A | 2/1994 | Lewis | 424/426 |
| 5,352,462 A | 10/1994 | Beck | 424/278.1 |
| 5,367,054 A | 11/1994 | Lee | 530/359 |
| 5,401,507 A | 3/1995 | Lewis | 424/426 |
| 5,419,910 A | 5/1995 | Lewis | 424/426 |
| 5,427,796 A | 6/1995 | Lewis | 424/426 |
| 5,650,175 A | 7/1997 | Beck et al. | 424/535 |
| 5,814,345 A | 9/1998 | Beck et al. | 424/535 |
| 5,863,561 A | 1/1999 | Beck et al. | 424/535 |
| 5,980,953 A | 11/1999 | Beck et al. | 424/535 |
| 6,054,124 A | 4/2000 | Beck et al. | 424/184.1 |
| 6,056,978 A | 5/2000 | Beck et al. | 424/535 |

FOREIGN PATENT DOCUMENTS

| | | | |
|---|---|---|---|
| EP | 0 127 712 | 1/1989 | A61K/7/32 |
| WO | WO 92/00756 | 1/1992 | A61K/39/35 |

OTHER PUBLICATIONS

Filler, S. J., et al., "Effect of Immune Bovine Milk on *Streptococcus mutans* in Human Dental Plaque," Archs Oral Biol 36:1, p. 41–47, 1991.

Gingerich, D.A., "Clinical and Pharmacologic Efficacy of Stolle Milk, Various Fractions, and WPI Plus," Stolle Milk Biologics International, Efficacy of Stolle Milk Fractions, p. 2–25, 1997.

Golay, A., et al., "Cholesterol–Lowering Effect of Skim Milk from Immunized Cows in Hypercholesterolemic Patients," Am J Clin Nutr, p. 1014–1019, 1990.

Davidson, et al., "Passive Immunisation of Children with Bovine Colostrum Containing Antibodies to Human Rotavirus," The Lancet, p. 709–712, 1989.

Ebina, T., et al., "Prevention of Rotavirus Infection by Oral Administration of Cow Colostrum Containing Antihuman-rotavirus Antibody," Med Microbiol Immunol 174, p. 177–185, 1985.

Ebina, T., et al., "Treatment of Multiple Sclerosis with Anti–Measles Cow Colostrum," Med Microbiol Immunol 173, p. 87–93, 1984.

"A Multicenter, Double–Blind, Placebo Controlled Study of Stolle Milk as Adjunct Therapy in Adult Rheumatoid Arthritis," Stolle Milk Biologics International, Rheumatoid Arthritis.

Beck, L. R., et al., "Milk Lymphocyte Anti–Adhesion Factor, and its Role as an Anti–Microbial, Indigenous Antimicrobial Agents of Milk—Recent Developments," Uppsala: International Dairy Federation, p. 62–72, 1993.

Berkow, R., The Merck Manual of Diagnosis and Therapy, p. 1792–93, 1805–07, 1992(16th Ed).

Hilpert, H., et al., "Use of Bovine Milk Concentrate Containing Antibody to Rotavirus to Treat Rotavirus Gastroenteritis in Infants," J of Infect Dis 156:1, p. 158–166, 1987.

Ishida, A., et al., "Administration of Milk From Cows Immunized with Intestinal Bacteria Protects Mice from Radiation–Induced Lethality," Biotherapy 5, p. 215–225, 1992.

Ishida, A. et al., "Consumption of Milk from Cows Immunized with Intestinal Bacteria Influences Age–Related Changes in Immune Competence in Mice," J Nutr 122, p. 1875–1883, 1992.

Kobayashi, T., et al., "Protective Effect of Orally Administering Immune Milk on Endogenous Infection in X–Irradiated Mice," Agric Biol Chem 55:9, p. 2265–2272, 1991.

Krick, G. et al., "Double Blind Controlled Trial on the Effect of Stolle Milk on Recovery After Excerise in Highly Trained Runners Protocal #RUN–1," Stolle R&D, RUN–01, Stolle Milk in Runners Final Report, p. 1–14, 1993.

McClead, R., et al., "Orally Administered Bovine Colostral Anti–Cholera Toxin Antibodies: Results of Two Clinical Trails," Am J of Med 85, p. 811–816, 1988.

Murosaki, S., et al., "Influence of Intake of Skim Milk from Cows Immunized with Intestinal Bacterial Antigens on Onset of Renal Disease in $(NZB \times NZW)F_1$ Mice Fed Ad Libitum or Restricted in Energy Intake," J. Nutr 121, p. 1860–1868, 1991.

(List continued on next page.)

Primary Examiner—Louise N. Leary
Assistant Examiner—Deborah K. Ware
(74) Attorney, Agent, or Firm—Sherrill Law Offices, PLLC

(57) ABSTRACT

Treatment of menorrhagia, hypermenorrhea and dysmenorrhea by the administration of a therapeutic amount of an antibacterial milk product.

20 Claims, No Drawings

OTHER PUBLICATIONS

Niedermeier, W., "Effects of Stolle Milk in Patients with Rheumatoid Arthritis: Double Blind, Placebo Controlled, Crossover Study," Stolle Milk Biologics International, Immune Milk in Arthritis Dr. Niedermeier Clinical Trail Summary, p. 1–6.

Nomoto, K., et al., "Antibacterial Effect of Bovine Milk Antibody Against *Escherichia coli* in a Mouse Indigenous Infection Model," Med Microbiol Immunol 181, p. 87–98, 1992.

Nord, J., et al., "Treatment with Bovine Hyperimmune Colostrum of Cryptosporidial Diarrhea in AIDS Patients," AIDS 4, p. 581–584, 1990.

Ormond, D. et al., "A Low Molecular Weight Component Derived from the Milk of Hyperimmunised Cows Suppresses Inflammation by Inhibiting Neutrophil Emigration," Agents Actions 37, p. 70–79, 1992.

Ormond, D. et al., "Milk from Hyperimmunized Dairy Cows as a Source of a Novel Biological Response Modifier," Agents Actions 38, p. C146–C149, 1993.

Ormond, D. et al., "The Anti–Inflammatory Activity of a Low Molecular Weight Component Derived from the Milk of Hyperimmunized Cows," Agents Actions 32, p. 160–166, 1991.

Owens, W. E., et al., "Effect of a Milk–Derived Factor on the Inflammatory Response to *Staphylococcus aureus* Intramammary Infection," Vet Immunol Immunopathol 30, p. 233–246, 1992.

Owens, W. E., et al., "Evaluation of an Anti–Inflammatory Factor Derived from Hyperimmunized Cows[1] (42832)," P.S.E.B.M. 190, p. 79–86, 1989.

Saxon, A., "Oral Administration of Bovine Colostrum Anti–Cyptosporidia Antibody Fails to Alter the Course of Human Cryptosporidiosis," J Parasit 73:2, p. 413–415, 1987.

Sharpe, S., et al., "Cholesterol–Lowering and Blood Pressure Effects of Immune Milk [1–3]," Am J Clin Nutr 59, p. 929–934, 1994.

Stelwagen K., et al., "An Anti–Inflammatory Component Derived from Milk of Hyperimmunised Cows Reduces Tight Junction Permeability in vitro," Inflamm Res 47, p. 384–388, 1998.

Stephan H. et al., "Antibodies form Colostrum in Oral Immunotherapy," J. Clin Chem Biochem 28, p. 19–23, 1990.

Tacket, C., et al., "Efficacy of Bovine Milk Immunoglobulin Concentrate in Preventing Illness After Shigella Flexneri Challenge," Am J Trop Med Hyg 47:3, p. 276–283, 1992.

Tacket, C., et al., "Protection by Milk Immunoglobin Concentrate Against Oral Challenging with Enterotoxigenic *Eschericha coli*," N Engl J Med 318:19, p. 1240–1243, 1988.

Tockman, M. et al., "Milk Drinking and Possible Protection of the Respiratory Epithelium," J Chron Dis 39:3, p. 207–209, 1986.

Tzipori, S. et al., "Remission of Diarrhoea Due to Cryptosporidiosis in an Immunodeficient Child Treated with Hyperimmune Bovine Colostrum," British Med J 293, p. 1276, 1986.

Ungar, B. et al., "Cessation of Cryptosporidium–Associated Diarrhea in an Acquired Immunodeficiency Syndrome Patient After Treatment with Hyperimmune Bovine Colostrum," Gastroenterology, 98:2, p. 486–489, 1990.

Woodman, R. et al, "The Effects of Hyperimmunised Milk Factor (HIMF) on Neutrophil Adhesion in vivo," Abstract, Soc Leukocyte Biol, 29th National Meeting Charleston S.C., 1992.

Thompson, L. et al. "The Effect of Fermented and Unfermented Milks on Serum Cholesterol," Am J Clin Nutr 36, p. 1106–1111, 1982.

"Isolation and Characterization of 3β–Hydroxy–Δ5–Steroids in Adrenal Carcinoma," *The Journal of Biological Chemistry*, vol. 234, No. 7, p. 1688–1692, Jul. 1959.

Zenk, J., Humantics HealthFacts: MicroLactin, Fall 1999.

Microbiological 7–and 15–Hydroxylations of C–19 Steroids, Journal of Steroid Biochemistry, vol. 9 p. 331–336, G. Defaye, M. J. Luche and E. M. Chambaz.

TREATMENT OF MENORRHAGIA, HYPERMENORRHEA, DYSMENORRHEA AND MENSTRUAL MIGRAINES BY THE ADMINISTRATION OF AN ANTIBACTERIAL MILK PRODUCT

BACKGROUND OF INVENTION

Many women suffer from menorrhagia, hypermenorrhea, dysmenorrhea, menstrual migraines and combinations thereof.

Menorrhagia is defined as excessive menstrual bleeding in the absence of organic pathology. Hypermenorrhea is defined as excessive duration of menstruation in the absence of organic pathology. Menorrhagia and hypermenorrhea have no known etiology. It has, however, been postulated that menorrhagia and hypermenorrhea are the result of an inappropriate exposure of the endometrium to hormones.

Menorrhagia is an exceedingly common problem, typically comprising approximately one in five outpatient referrals to gynecological departments. Women suffering severe menorrhagia are at risk for chronic anemia. Hypermenorrhea is also an exceedingly common problem.

Dysmenorrhea is a term used to describe painful menstruation. The pain may range from minor cramping to intense pain accompanied by diarrhea, nausea and vomiting, with sensations of pelvic heaviness and breast fullness.

Menstrual migraines is a term used to describe migraines which accompany menstruation.

Mankind has sought ways to treat menorrhagia, hypermenorrhea, dysmenorrhea and menstrual migraines, including efforts ranging from the consumption of specific foods to drug therapy such as treatment with oral contraceptives or progestin. While certain of these techniques have demonstrated limited success in decreasing the severity of menorrhagia, hypermenorrhea, dysmenorrhea and/or menstrual migraines, the search continues for drug-free alternatives.

SUMMARY OF INVENTION

I have discovered that menorrhagia, hypermenorrhea, dysmenorrhea and menstrual migraines can be treated by administering a therapeutic amount of an antibacterial milk product.

DETAILED DESCRIPTION

Definitions

As utilized herein, the phrase antibacterial milk product means antibacterial milk obtained in accordance with the process set forth in U.S. Reissue Pat. No. Re. 33,565, the disclosure of which is hereby incorporated by reference, and any active fraction of such antibacterial milk, including specifically, but not exclusively, skimmed antibacterial milk, antibacterial powdered whole milk, antibacterial skimmed powdered milk, concentrated antibacterial powdered whole milk, and concentrated antibacterial skimmed powdered milk.

As utilized herein, the phrase active fraction, when used in connection with antibacterial milk, means a preparation or composition extracted from the antibacterial milk which retains the desired therapeutic property of the unextracted antibacterial milk due to the presence of derivatized and processed forms of the allergens used to immunize the animal providing the antibacterial milk.

As utilized herein, the phrase antibacterial powdered milk means antibacterial milk obtained in accordance with the process set forth in U.S. Reissue Pat. No. Re. 33,565, which has optionally been skimmed to remove fat and has been dried to form a powdered milk.

As utilized herein, the phrase antibacterial powdered skimmed milk means antibacterial milk obtained in accordance with the process set forth in U.S. Reissue Pat. No. Re. 33,565, which has been skimmed to remove fat and has been dried to form a powdered milk.

As utilized herein, the phrase concentrated antibacterial powdered milk means antibacterial powdered milk which has optionally been skimmed to remove fat, separated to remove lactose and salt, and dried to form a concentrated powdered milk.

As utilized herein, the phrase concentrated antibacterial powdered skimmed milk means antibacterial powdered milk which has been skimmed to remove fat, separated to remove lactose and salt, and dried to form a concentrated powdered milk.

Antibacterial Milk Product

Antibacterial milk, from which various antibacterial milk products can be extracted, can be produced in accordance with the process set forth in U.S. Reissue Pat. No. Re. 33,565, the disclosure of which is hereby incorporated by reference. A synopsis of the process, as described in U.S. Reissue Pat. No. Re. 33,565, is provided below.

Preparation of the Vaccine

The bacteria strains listed in Table One, obtained from the American Type Culture Collection, are individually grown on a blood agar plate to test the viability of the culture and determine if growth pattern is typical or atypical of the bacteria in question. A single colony from each of the test cultures is taken for histological examination to further ensure authenticity and purity of the culture. A single colony of each culture is used to inoculate 500 ml of standard culture broth as recommended by the American Type Culture Collection.

TABLE ONE

[t2]
Bacterial Antigens

| ORGANISM | *ATCC NO. |
|---|---|
| Staphylococcus aureus | 11631 |
| Staphylococcus epidermidis | 155 |
| Streptococcus pyogenes A. Type 1 | 8671 |
| Streptococcus pyogenes A. Type 3 | 10389 |
| Streptococcus pyogenes A. Type 5 | 12347 |
| Streptococcus pyogenes A. Type 8 | 12349 |
| Streptococcus pyogenes A. Type 12 | 11434 |
| Streptococcus pyogenes A. Type 14 | 12972 |
| Streptococcus pyogenes A. Type 18 | 12357 |
| Streptococcus pyogenes A. Type 22 | 10403 |
| Aerobacter aerogenes | 884 |
| Escherichia coli | 26 |
| Salmonella enteritidis | 13076 |
| Pseudomonas aeruginosa | 7700 |
| Klebsiella pneumoniae | 9590 |
| Salmonella typhimurium | 13311 |
| Haemophilus influenzae | 9333 |
| Streptococcus mitis | |
| Proteus vulgaris | 13315 |
| Shigella dysenteriae | 11835 |
| Diplococcus pneumoniae | |
| Propionibacter acnes | |
| Streptococcus sanguis | |
| Streptococcus salivarius | |

TABLE ONE-continued

[t2]
Bacterial Antigens

| ORGANISM | *ATCC NO. |
|---|---|
| *Streptococcus mutans* | |
| *Streptococcus agalactiae* | |

All organisms are incubated as static cultures with the exception of *Escherichia coli, Salmonella enteritdis, Pseudomonas aeruginosa* and *Salmonella typhimurium*, which are incubated in a shaker to provide agitation. Identification of bacterial strains and the American Type Culture Collection catalog numbers are shown in Table One. Each culture is cultivated for 48 hours at 37° C. Following incubation, the cultures are killed by heating at 60° C. for two hours. Samples of the killed bacteria are used to inoculate fresh broth, which is then incubated for 24 hours at 37° C. to confirm that the killing process was complete. Only cultures proven sterile by this procedure are used for further processing. Sterile cultures are washed five times in distilled water and the cells recovered by centrifugation. The bacterial cells are frozen by immersion in liquid nitrogen and freeze-dried by lyophilization. The lyophilized cells are stored in sterile vials until used for production of the polyvalent vaccine.

A polyvalent vaccine is prepared by weighing out one gram quantities of each of the bacterial strains. The dry cells were mixed together and this mixture is suspended in sterile physiological saline (20 grams of bacteria per 500 ml saline).

A sample of the concentrated solution is diluted in serial fashion with saline to determine the dilution, which gives a concentration of $4 \times 10^8$ CL per cc. The stock concentrated polyvalent vaccine is dispersed into multiple containers and stored frozen. A sufficient amount of concentrated antigen is included in each individual container to immunize 50 cows. The final dilution of concentrate is made just prior to immunization. The preferred procedure is to remove a sufficient number of vials to immunize the number of cows to be treated. For example, the vials are removed 24 hours prior to the planned time of immunization; a sample of the concentrate is then diluted in a sterile container to a final concentration of $4 \times 10^8$ cells per ml. The maximum response in cows is obtained by injecting $20 \times 10^8$ bacterial cells or 5 cc of the sterile preparation, which is $4 \times 10^8$ cells per ml according to the method on immunization described below.

Preferred Process for Immunization of Cows

Cows are injected with 5 cc of polyvalent antigen containing $20 \times 10^8$ bacterial cells. The injection is made intramuscularly in the gluteus maximus muscle of the hind leg. This procedure is repeated at one-week intervals for four consecutive weeks beginning 2–3 weeks prior to the predicted day of parturition. Following the primary immunization, booster injections using the same concentration of the antigen are given every 14 days. This method of immunization gives the maximum antibody titer.

Collection, Handling and Processing of Milk

The milk is collected from immunized cows in a modern dairy parlor. A fully automated milking system collects and stores the milk under complete sanitary conditions. The milking system consists of automated machines connected directly to refrigerated storage tanks by a closed system of pipes. The complete system is cleaned and sterilized following each milking to ensure maximum sanitary conditions. It is important to take careful steps to prevent the growth of bacteria in the antibacterial milk during processing, since such bacteria can lower the concentration of proteins in the milk.

Milk is transported daily from the refrigerated holding tanks to a dairy processing plant by milk transport trucks. At the dairy plant, a high temperature short-time system is used to pasteurize the antibacterial milk. Specialized dairy machinery provides the flash heating of a continuous flow of milk to 155° F. for a period of not more than 15 seconds. Temperature and time is critical since proteins are susceptible to degradation by heat. Milk proteins are destroyed at temperature above 165° F. if held for periods longer than one minute.

Following pasteurization, the whole milk is immediately cooled, fat is removed by centrifugation to produce skimmed antibacterial milk, and the skimmed antibacterial milk is powdered by a spray-drying process. The spray-drying process consists of a large drying chamber into which hot air (350° F.) is blown at high velocity. The skimmed milk is atomized into the chamber where the finely divided milk particle are instantly dried as they fall to the bottom of the tank. The dried milk is removed automatically by means of mechanical devices and the milk powder is packaged under sanitary conditions. Prior to atomizing, the skimmed milk is condensed by boiling in a chamber under vacuum at a temperature of 100 to 110° F. At each step, it is critical to keep bacteria from contaminating the milk since this reduces the concentration of milk proteins.

Concentration of Milk

A concentrated form of the antibacterial milk in which about 95% of the lactose and salt is removed can be obtained by ultrafiltration of the pasteurized skimmed antibacterial milk through a membrane or molecular sieve that retards molecules with a molecular weight of greater than 100,000 as set forth in U.S. Pat. No. 5,106,618, the disclosure of which is hereby incorporated by reference. Since immunoglobulins have molecular weights well in excess of 100,000 while lactose has a molecular weight well below 100,000, lactose is effectively separated from the immunoglobulin milk proteins. This permits a 10 to 100 fold concentration, typically about a 30 fold concentration, of the milk proteins.

Such concentration of the antibacterial milk reduces the mass to such an extent that capsules containing an effective amount of the milk proteins can be formulated from concentrated antibacterial powdered skimmed milk.

Commercial Availability of Antibacterial Milk Products

Concentrated antibacterial powdered skimmed milk, manufactured in accordance with the process described above and useful in the treatment of menorrhagia, hypermenorrhea, dysmenorrhea and menstrual migraines in accordance with the treatment method disclosed herein, is commercially available from AdvantRx Corporation of Chanhassen, Minnesota and Stolle Milk Biologics, Inc. of Cincinnati, Ohio under the mark MicroLactin™.

Administration

Administration Route

The antibacterial milk product can be administered by virtually any of the commonly accepted practices for the administration of pharmaceutical preparations including specifically, but not exclusively, mucosal administration, oral consumption, ocular administration, subcutaneous injection, transdermal administration, etc.

Mucosal administration of the antibacterial milk product includes such routes as buccal, endotracheal, nasal, pharyngeal, rectal, sublingual, vaginal, etc. For administration through the buccal/sublingual/pharyngeal/endotracheal mucosa, the antibacterial milk product may be formulated as an emulsion, gum, lozenge, spray, tablet or an inclusion complex such as cyclodextrin inclusion complexes. Nasal administration is conveniently conducted through the use of a sniffing power or nasal spray. For rectal and vaginal administration the antibacterial milk product may be formulated as a cream, douch, enema or suppository.

Oral consumption of the antibacterial milk product may be effected by incorporating the antibacterial milk product into a food or drink, or formulating the antibacterial milk product into a chewable or swallowable tablet.

Ocular administration may be effected by incorporating the antibacterial milk product into a solution or suspension adapted for ocular application such as drops or sprays.

Subcutaneous administration involves incorporating the antibacterial milk product into a pharmaceutically acceptable and injectable carrier.

For transdermal administration, the antibacterial milk product may be conveniently incorporated into a lipophilic carrier and formulated as a topical creme or adhesive patch.

Oral administration is preferred due to ease of administration and cost.

Dose Rate

The range of dosages and dose rates effective for achieving the desired biological properties and characteristics may be determined in accordance with standard industry practices. These ranges can be expected to differ depending upon whether the desired response is the prophylactic, modulatory, ameliorative or curative in nature.

Generally, daily oral administration of about 45 to about 90 grams of antibacterial powdered skimmed milk, or about 1 to about 4 grams of concentrated antibacterial powdered skimmed milk should be effective. Alternatively, the antibacterial low-fat milk product may be administered only during menstruation.

Experimental

Experiment 1

One female subject, age 41, afflicted with moderate menorrhagia, hypermenorrhea and dysmenorrhea and severe menstrual migraines orally consumed two 500 mg capsules of MicroLactin™ twice daily (hereinafter MicroLactin™ Treatment Regimen) for four (4) months. She reported a significant decrease in both the duration and amount of menstruation, a lessening of menstrual cramping and a complete absence of menstrual migraines while on the MicroLactin™ Treatment Regimen. She then discontinued the MicroLactin™ Treatment Regimen upon the conclusion of menstruation in the fourth month and reported a return to pretreatment conditions in the duration and amount of menstruation, severity of menstrual cramping and occurrence of a debilitating menstrual migraine during the untreated menstruation. She restarted the MicroLactin Treatment Regimen shortly after completion of her untreated menstruation and again reported a significant decrease in both the duration and amount of menstruation, a lessening of menstrual cramping and a complete absence of menstrual migraines during subsequent menstruations.

What is claimed is:

1. A treatment method comprising the step of administering to a female mammal suffering from menorrhagia a therapeutic amount of an antibacterial milk product.

2. The method of claim 1 wherein the step of administering the antibacterial milk product to a female mammal comprises the step of administering the antibacterial milk product to a female human.

3. The method of claim 2 wherein the step of administering the antibacterial milk product comprises the step of orally administering the antibacterial milk product.

4. The method of claim 3 wherein the step of orally administering the antibacterial milk product comprises the step of orally administering a powdered antibacterial milk product.

5. The method of claim 3 wherein the step of orally administering the antibacterial milk product comprises the step of orally administering a concentrated powdered antibacterial milk product.

6. A treatment method comprising the step of administering to a female mammal suffering from hypermenorrhea a therapeutic amount of an antibacterial milk product.

7. The method of claim 6 wherein the step of administering the antibacterial milk product to a female mammal comprises the step of administering the antibacterial milk product to a female human.

8. The method of claim 7 wherein the step of administering the antibacterial milk product comprises the step of orally administering the antibacterial milk product.

9. The method of claim 8 wherein the step of orally administering the antibacterial milk product comprises the step of orally administering a powdered antibacterial milk product.

10. The method of claim 8 wherein the step of orally administering the antibacterial milk product comprises the step of orally administering a concentrated powdered antibacterial milk product.

11. A treatment method comprising the step of administering to a female mammal suffering from dysmenorrhea a therapeutic amount of an antibacterial milk product.

12. The method of claim 11 wherein the step of administering the antibacterial milk product to a female mammal comprises the step of administering the antibacterial milk product to a female human.

13. The method of claim 12 wherein the step of administering the antibacterial milk product comprises the step of orally administering the antibacterial milk product.

14. The method of claim 13 wherein the step of orally administering the antibacterial milk product comprises the step of orally administering a powdered antibacterial milk product.

15. The method of claim 13 wherein the step of orally administering the antibacterial milk product comprises the step of orally administering a concentrated powdered antibacterial milk product.

16. A treatment method comprising the step of administering to a female mammal suffering from menstrual migraines a therapeutic amount of an antibacterial milk product.

17. The method of claim 16 wherein the step of administering the antibacterial milk product to a female mammal comprises the step of administering the antibacterial milk product to a female human.

18. The method of claim 17 wherein the step of administering the antibacterial milk product comprises the step of orally administering the antibacterial milk product.

19. The method of claim 18 wherein the step of orally administering the antibacterial milk product comprises the step of orally administering a powdered antibacterial milk product.

20. The method of claim 18 wherein the step of orally administering the antibacterial milk product comprises the step of orally administering a concentrated powdered antibacterial milk product.

* * * * *